US00PP31401P2

(12) United States Plant Patent
de Groot

(10) Patent No.: US PP31,401 P2
(45) Date of Patent: Jan. 28, 2020

(54) *ROSA* 'RUIRE0126A'

(50) Latin Name: *Rosa hybrida*
Varietal Denomination: RUIRE0126A

(71) Applicant: Hendrikus Cornelis Adrianus de Groot, Amstelveen (NL)

(72) Inventor: Hendrikus Cornelis Adrianus de Groot, Amstelveen (NL)

(73) Assignee: De Ruiter Intellectual Property BV (NL)

( * ) Notice: Subject to any disclaimer, the term of this patent is extended or adjusted under 35 U.S.C. 154(b) by 0 days.

(21) Appl. No.: 16/350,982

(22) Filed: Feb. 7, 2019

(51) Int. Cl.
*A01H 5/02* (2018.01)
*A01H 6/74* (2018.01)

(52) U.S. Cl.
USPC ..... Plt./148

(58) Field of Classification Search
USPC ..... Plt./148
CPC ..... A01H 5/02; A01H 6/74
See application file for complete search history.

*Primary Examiner* — Annette H Para
(74) *Attorney, Agent, or Firm* — Cassandra Bright

(57) ABSTRACT

A new and distinct hybrid *Rosa* cultivar named 'RUIRE0126A' is disclosed, characterized by large, pink, double flowers with a light floral fragrance, and glossy foliage. Plants are upright, and exhibit good resistance to blackspot diseases. The new variety is a *Rosa*, normally produced as all outdoor garden or container plant.

2 Drawing Sheets

Latin name of the genus and species: *Rosa hybrida.*
Variety denomination: 'RUIRE0126A'.

BACKGROUND OF THE INVENTION

The new *Rosa* cultivar is a product of a planned breeding program conducted by the inventor. The cross resulting in this new variety was made during Spring of 2004, by the inventor at a research nursery in Hazerswoude, The Netherlands.

The seed parent is the unpatented variety *Rosa* 'NOACAS'. The pollen parent is an unnamed, patented proprietary *Rosa* variety. The new variety was selected in June 2005 by the inventor at the same research nursery in Hazerswoude, The Netherlands. The inventor continued observing characteristics of the new variety for several years, in the controlled conditions of the research nursery.

Asexual reproduction of the new cultivar was performed by vegetative softwood cuttings. This was first performed at a greenhouse in Hazerswoude, The Netherlands, in August 2005, and has shown that the unique features of this cultivar are stable and reproduced true to type in successive generations.

SUMMARY OF THE INVENTION

The cultivar 'RUIRE0126A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUIRE0126A' These characteristics in combination distinguish 'RUIRE0126A' as a new and distinct *Rosa* cultivar:

1. Double flowers.
2. Large pink flowers.
3. Glossy foliage.

PARENTAL COMPARISON

Plants of the new cultivar 'RUIRE0126A' are similar to plants of the seed parent, in most horticultural characteristics, however, plants of the new cultivar 'RUIRE0126A' differ in the following:

1. The new variety has pink flowers, while the seed parent has orange flowers.

Plants of the new cultivar 'RUIRE0126A' are similar to plants of the pollen parent in most horticultural characteristics, however, plants of the new cultivar 'RUIRE0126A' differs in the following;

1. The new variety has larger pink flowers than the pollen parent.

COMMERCIAL COMPARISON

Plants of the new cultivar 'RUIRE0126A' can be compared to the commercial variety *Rosa* 'ZLEMarianneYoshida', U.S. Plant Pat. No. 22,205. These varieties are similar in most horticultural characteristics, however 'RUIRE0126A' differs in the following:

1. This new cultivar has larger flowers than this comparator.
2. This new cultivar has larger leaves than this comparator.
3. The new variety has a less ruffled petals than this comparator.

BRIEF DESCRIPTION OF THE PHOTOGRAPHS

Figure 1:
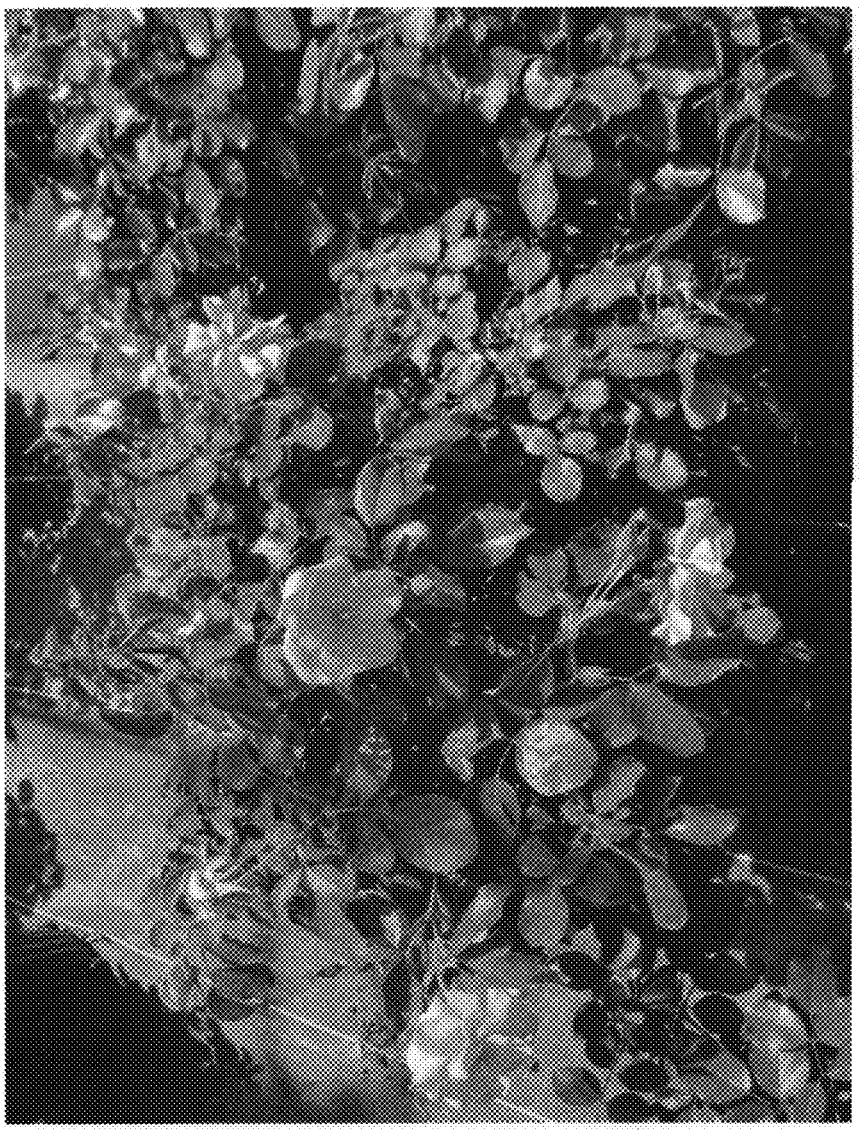

The accompanying photograph in FIG. 1 illustrates in full color a typical plant of 'RUIRE0126A' in a 2 gallon con tainer grown in Grand Haven, Mich. in a polyhouse. Plants in FIG. 1 are approximately 2 to 3 years old.

Figure 2:
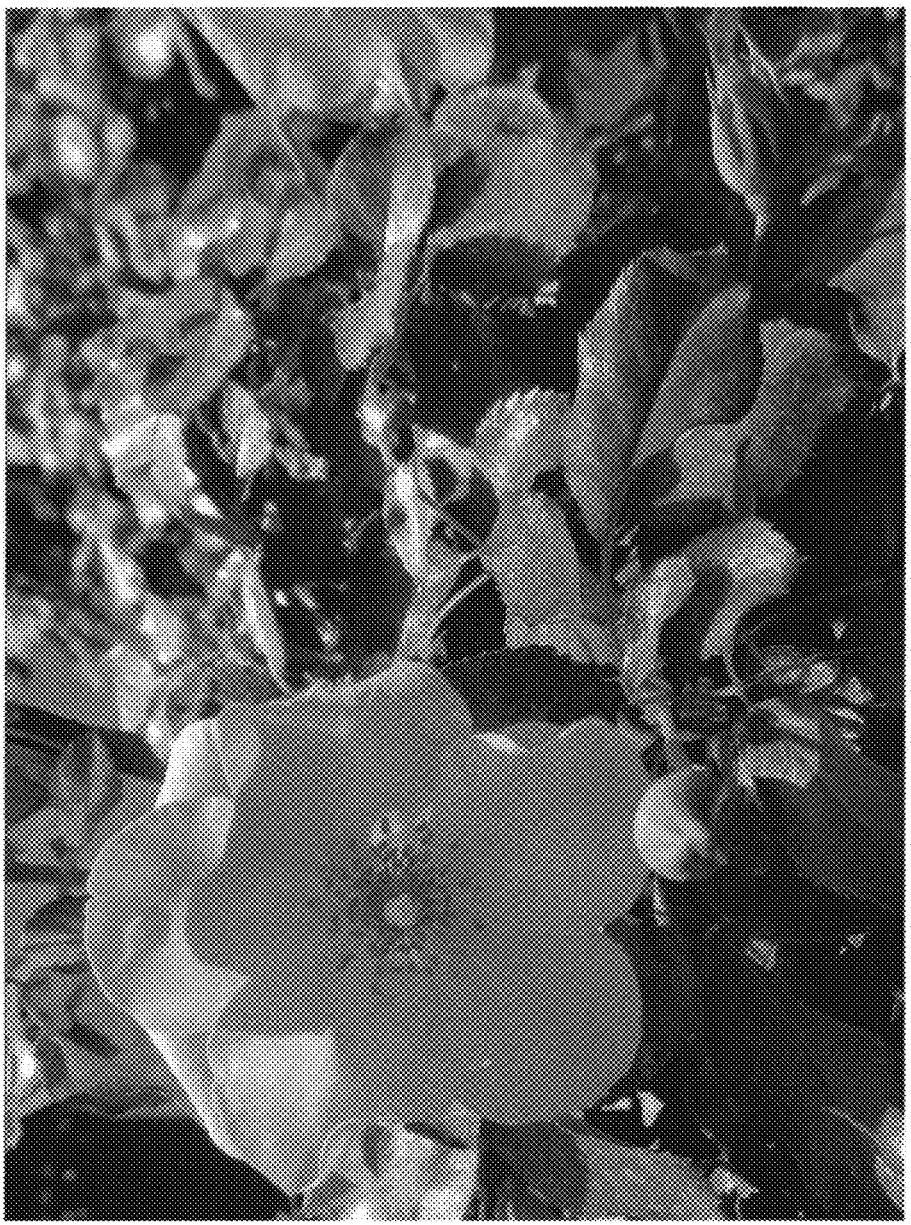

FIG. 2 illustrates a close up view of a flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RUIRE0126A' plants grown outdoors, in Hazerswoude, The Netherlands. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.
Botanical classification: *Rosa* 'RUIRE0126A'.
Market classification: Garden floribunda.

PROPAGATION

Time to initiate roots: 30 days at approximately 20° C.
Time to produce a rooted cutting: 120 days.
Root description: Fibrous and fleshy, dense, medium thickness, moderately branched. White in color, not accurately measured by R.H.S. chart.

PLANT

Age of plant described: 2-3 years.
Growth habit: Upright, mounded.
Container size: 1, 2, 3, 5 gallon pots.
Height: 51 cm.
Plant spread: 60 cm.
Rootstock: Own root.
Growth rate: Moderate.
Branching habit: Basal.
Length of primary lateral branches: 30 to 48 cm.
Diameter of lateral branches: 3 mm.
Quantity lateral branches: 19.
Internode length: 2-6 cm.
Stem:
- *Shape*.—Round, thorny.
- *Aspect*.—Upright.
- *Strength*.—Strong.
- *Color*.—RHS Green 139C.
- *Pubescence*.—None.

Thorns:
- *Number per linear centimeter*.—2.
- *Shape*.—Narrow deltoid, bent downward.
- *Apex*.—Acicular.
- *Base*.—Obtuse.
- *Height*.—1 cm.
- *Color, immature*.—RHS Yellow-Green 144B.
- *Color, mature*.—RHS Green 137B near stem; Greyed-Orange 177C near tip.

FOLIAGE

Leaf:
- *Arrangement*.—Alternate.
- *Quantity*.—5 to 8 per lateral branch.
- *Average length*.—7-8.5 cm.
- *Average width*.—6.75 cm.

Leaflet:
- *Quantity*.—3 to 7 per leaf.
- *Terminal length*.—4.5 cm.
- *Terminal width*.—2.5 cm.
- *Lateral length*.—2.75-3.5 cm.
- *Lateral width*.—1.75-2.5 cm.
- *Shape*.—Obovate.
- *Apex*.—Acute.
- *Base*.—Rounded.
- *Margin*.—Serrate.
- *Pubescence*.—None.
- *Texture*.—Smooth, glossy.
- *Color*.—Young foliage upper side: RHS Yellow-Green 144A; margin Greyed-Purple 183A. Young foliage under side: RHS Yellow-Green 144A with some Greyed-Red 180A. Mature foliage upper side: Near RHS Green N134A. Mature foliage under side: RHS Green 137C.
- *Venation*.—Type: Pinnate. Young Venation color upper side: RHS Greyed-Orange 168B. Mature Venation color upper side: RHS Greyed-Yellow 162A. Young Venation color under side: RHS Greyed-Orange 168B. Mature Venation color under side: RHS Greyed-Yellow 162A.

Petiole:
- *Leaf petiole length*.—1.5 cm.
- *Leaf petiole diameter*.—3 mm.
- *Leaflet petiole length*.—3 mm.
- *Leaflet petiole diameter*.—1 mm.
- *Leaf petiole texture*.—Micro-thorns.
- *Leaflet petiole texture*.—Smooth.
- *Leaf petiole color, upper surface*.—RHS Greyed-Yellow 161A
- *Leaf petiole color, lower surface*.—RHS Yellow-Green N144A.
- *Leaflet petiole color, immature, upper surface*.—RHS Greyed-Orange 176A.
- *Leaflet petiole color, immature, lower surface*.—RHS Yellow-Green 145A.
- *Leaflet petiole color, mature, upper surface*.—RHS Greyed-Orange 175B.
- *Leaflet petiole color, mature, lower surface*.—RHS Greyed-Yellow 162A.

Stipule:
- *Margin*.—Ciliate.
- *Length*.—1.5 cm.
- *Width*.—2 mm.
- *Texture, upper surface*.—Ciliate.
- *Texture, lower surface*.—Smooth.
- *Color, upper surface*.—RHS Green 134A.
- *Color, lower surface*.—RHS Green 134B.

FLOWER

Natural flowering season: Spring through Summer.
Flower type and habit: Double, rotate.
Quantity of flowers: 1 to 4 per spray.
Sprays per lateral stem: 1 to 3.
Flower:
- *Shape*.—Rotate, double whorl.
- *Diameter*.—7 cm.
- *Height*.—4 cm.
- *Aspect*.—Outward.
- *Persistent or self-cleaning*.—Self-cleaning.
- *Fragrance*.—Light, floral.

Peduncle:
*Length.*—2 to 3.5 cm.
*Diameter.*—1.5 cm.
*Angle.*—Outward, 45-90 degrees.
*Strength.*—Strong.
*Texture.*—Smooth.
*Color.*—RHS Yellow-Green 144B.

Petals:
*Petal arrangement.*—Double whorl.
*Appearance.*—Vibrant, recurved, rounded with notch in center.
*Petal quantity.*—12 to 16.
*Fused.*—No.
*Length.*—2-3.5 cm.
*Width.*—3.25 cm.
*Shape.*—Obovate.
*Margin.*—Entire.
*Apex.*—Retuse.
*Base.*—Obtuse.
*Texture.*—Smooth, silky.
*Color.*—When opening: Upper surface: RHS Red 52A. Lower surface: RHS Red 52A. Fully opened: Upper surface: RHS Red-Purple 67D. Lower surface: Near RHS Red-Purple N66.

Petaloid:
*Appearance.*—Irregular, curved.
*Arrangement.*—Whorled.
*Number.*—0 to 4.
*Shape.*—Irregular orbicular.
*Margin.*—Entire.
*Length.*—2.5 cm.
*Width.*—1.5 to 2.5 cm.
*Color.*—Immature: RHS Red 52A. Mature: RHS Red-Purple 67D.

Bud:
*Shape.*—Ovate.
*Length.*—2 cm.
*Diameter.*—1 cm.
*Color.*—RHS Green 143B.

Sepals:
*Quantity.*—5.
*Length.*—2.5 cm.
*Width.*—6 mm.
*Shape.*—Long, very narrow deltoid.
*Apex.*—Acuminate.
*Base.*—Truncate.
*Margin.*—Pubescent, irregular, narrow teeth.
*Color.*—Immature, Upper Side: RHS Green 140D. Immature, Under Side: RHS Green 140A. Mature, Upper Side: RHS Green 141C. Mature, Under Side: RHS Green 140A.
*Texture.*—Smooth, pubescent all surfaces.

Peduncle:
*Length.*—2 to 3.5 mm.
*Diameter.*—1.5 mm.
*Angle.*—Outward, 45-90 degrees.
*Strength.*—Strong.
*Texture.*—Smooth.
*Color.*—RHS Yellow-Green 144B.

Receptacle:
*Length.*—5 mm.
*Width.*—5 mm.
*Shape.*—Obovate.
*Texture.*—Smooth.
*Color.*—RHS Green 140A.

REPRODUCTIVE ORGANS

Stamens:
*Quantity.*—Average 100.
*Filament length.*—Average 9 mm
*Filament color.*—RHS Red 54D.

Anthers:
*Length.*—1 mm.
*Shape.*—Club-like.
*Color.*—RHS Yellow-Orange 17A.
*Pollen.*—Color: RHS Yellow-Orange 17A. Quantity: Moderate.

Pistil:
*Number.*—20.
*Length.*—5-7 mm.

Stigma:
*Shape.*—Linear, clustered.
*Color.*—RHS Yellow 13B.

OTHER CHARACTERISTICS

Seeds and fruits: Not observed.

Disease/pest resistance: Good overall disease resistance to normal pests and diseases typical of garden roses. Very good resistance to blackspot diseases.

What is claimed is:

1. A new and distinct hybrid cultivar of *Rosa* plant named 'RUIRE0126A' as herein illustrated and described.

* * * * *